(12) United States Patent
Bjork, Jr.

(10) Patent No.: US 9,339,593 B2
(45) Date of Patent: *May 17, 2016

(54) DRUG-ELUTING CORONARY ARTERY STENT COATED WITH ANTI-PLATELET-DERIVED GROWTH FACTOR ANTIBODIES OVERLAYING EXTRACELLULAR MATRIX PROTEINS WITH AN OUTER COATING OF ANTI-INFLAMMATORY (CALCINEURIN INHIBITOR) AND/OR ANTI-PROLIFERATIVES

(76) Inventor: Robert L. Bjork, Jr., San Diego, CA (US)

(*) Notice: Subject to any disclaimer, the term of this patent is extended or adjusted under 35 U.S.C. 154(b) by 99 days.

This patent is subject to a terminal disclaimer.

(21) Appl. No.: 12/344,125

(22) Filed: Dec. 24, 2008

(65) Prior Publication Data

US 2009/0157173 A1    Jun. 18, 2009

Related U.S. Application Data

(63) Continuation-in-part of application No. 11/972,540, filed on Jan. 10, 2008, now abandoned.

(60) Provisional application No. 60/880,420, filed on Jan. 11, 2007, provisional application No. 60/901,338, filed on Feb. 13, 2007, provisional application No. 61/042,174, filed on Apr. 3, 2008, provisional application No. 61/006,309, filed on Jan. 3, 2008.

(51) Int. Cl.
*A61F 2/02* (2006.01)
*A61F 2/06* (2013.01)
*A61L 31/10* (2006.01)
(Continued)

(52) U.S. Cl.
CPC . *A61L 31/10* (2013.01); *A61F 2/91* (2013.01);
*A61L 31/16* (2013.01); *A61F 2230/0054* (2013.01); *A61F 2250/0067* (2013.01); *A61F 2310/00976* (2013.01); *A61L 2300/252* (2013.01); *A61L 2300/256* (2013.01); *A61L 2300/41* (2013.01); *A61L 2300/416* (2013.01);
(Continued)

(58) Field of Classification Search
CPC ..................................... A61F 2/02; A61F 2/06
USPC ................................................ 623/1.41–1.46
See application file for complete search history.

(56) References Cited

U.S. PATENT DOCUMENTS 5,551,954 A    9/1996  Buscemi et al.
5,609,629 A *  3/1997  Fearnot et al. ............... 623/1.42
(Continued)

OTHER PUBLICATIONS

Zhao et al., A Novel Biodegradable Polymer Modified With Peptide For Drug Eluting Stent, The American Journal of Cardiology, Oct. 20-25, 2007, TCT Abstracts/Electronic, TCT 420.

(Continued)

*Primary Examiner* — Yashita Sharma
(74) *Attorney, Agent, or Firm* — DLA Piper LLP (US)

(57) ABSTRACT

The present invention relates to a combination of agents, including an anti-proliferative agent, an anti-inflammatory agent, an anti-growth factor, and an extracellular matrix (ECM) molecule coated on a stent to prevent acute and sub-acute thrombosis, enhance endothelial in-growth, and prevent neointimal hyperplasia, and/or suppress neovascularization, and thereby reduce restenosis rates for drug eluting stents. The present invention also relates to methods of using such multiple drug eluting stents for the treatment of heart disease and other vascular conditions.

13 Claims, 3 Drawing Sheets

(51) Int. Cl.
*A61F 2/91* (2013.01)
*A61L 31/16* (2006.01)

(52) U.S. Cl.
CPC .......... *A61L 2300/42* (2013.01); *A61L 2300/61* (2013.01)

(56) References Cited

U.S. PATENT DOCUMENTS

| | | | |
|---|---|---|---|
| 5,648,076 A | 7/1997 | Ross et al. | |
| 6,315,794 B1* | 11/2001 | Richter | 623/1.34 |
| 6,656,966 B2 | 12/2003 | Garvey et al. | |
| 6,786,927 B2 | 9/2004 | Pallikaris et al. | |
| 6,861,088 B2 | 3/2005 | Weber et al. | |
| 7,008,979 B2 | 3/2006 | Schottman et al. | |
| 7,041,127 B2 | 5/2006 | Ledergerber | |
| 7,208,172 B2 | 4/2007 | Birdsall et al. | |
| 7,223,286 B2 | 5/2007 | Wright et al. | |
| 7,225,518 B2 | 6/2007 | Eidenschink et al. | |
| 7,264,822 B2 | 9/2007 | Shalaby et al. | |
| 7,279,175 B2 | 10/2007 | Chen et al. | |
| 7,284,401 B2 | 10/2007 | Larson et al. | |
| 7,314,480 B2 | 1/2008 | Eidenschink et al. | |
| 7,351,421 B2* | 4/2008 | Sung et al. | 424/422 |
| 2001/0037144 A1 | 11/2001 | Kim et al. | |
| 2003/0036794 A1* | 2/2003 | Ragheb et al. | 623/1.42 |
| 2003/0060871 A1* | 3/2003 | Hill et al. | 623/1.15 |
| 2005/0079200 A1* | 4/2005 | Rathenow et al. | 424/423 |
| 2005/0149175 A1* | 7/2005 | Hunter et al. | 623/1.42 |
| 2006/0135476 A1 | 6/2006 | Kutryk et al. | |
| 2006/0224234 A1 | 10/2006 | Jayaraman | |

OTHER PUBLICATIONS

Manoukian et al., Major Bleeding is Associated with Increased One-Year Mortality and Ischemic Events in Patients with Acute Coronary Syndromes Undergoing Percutaneous Coronary Intervention: The ACUITY Trial, The American Journal of Cardiology, 10/20-.

Toutouzas et al., Long Term Results From The First-in-man Application of Bevacizumab-eluting Stent: A Novel Approach For the Inhibition Of Plaque Neovascularization, The American Journal of Cariology, Oct. 20-25, 2007, TCT.

Hakimimehr et al., In-Vitro Evaluation of a Novel Dual-Drug Eluting Stent to Target Inflammation and Proliferation Following Stent Implantation, The American Journal of Cardiology, Oct. 20-25, 2007, TCT Abstracts/Electronic, TCT 399.

Mavromatis et al., Systemic Inflammatory Activation and Endothelial Repair After Stenting: A Comparison of Drug-Eluting Stents with Bare Metal Stents, The American Journal of Cardiology, Oct. 20-25, 2007, TCT Abstracts/Electronic, TCT 443.

Ellis et al., Long-term Safety and Clinical Efficacy Outcomes of the Paclitaxel-Eluding Stent from a Patient-level Meta-Analysis of the TAXUS Clinical Trials, The American Journal of Cardiology, Oct. 20-25, 2007, TCT Abstracts/Electronic, TCT 534.

Lee et al., Long-Term Clinical Outcomes and Stent Thrombosis After Drug-Eluting Stent and Versus Bare-Metal Stent for Acute Myocardial Infarction, The American Journal of Cardiology, Oct. 20-25, 2007, TCT Abstracts/Electronic, TCT 551.

Hergenrother et al., In Vivo Performance of New Biodegradable Stent Coating Materials in a Porcine Coronary Model, The American Journal of Cardiology, Oct. 20-25, 2007, TCT Abstracts/Electronic, TCT 406.

Martin-Yuste et al., Safety of Genous Stent Implantation in Patients with High Risk of Bleeding. A Single-Center Prospective Registry, The American Journal of Cardiology, Oct. 20-25, 2007, TCT Abstracts/Electronic, TCT 412.

Nakamura et al., Drug-Eluting Stents for the Treatment of Very Long Coronary Artery Stenosis: A Comparison with Sirolimus, Paclitaxel, Zotarolimus, Tacrolimus-Eluting Stent and EPC Capture Stent: Multicenter Registry in Asia, The American Journal of Cardiology.

Lasave et al., Comparative Analysis of the Overlap Segment of Sirolimus-Eluting versus Zotarolimus-Eluting Stents: A Tridimensional Intravascular Ultrasound Study, The American Journal of Cardiology, Oct. 20-25, 2007, TCT Abstracts/Electronic, TCT 403.

Jensen et al., Neointimal Hyperplasia and Peri-Stent Remodeling after Sirolimus-Eluting or Paclitaxel-Eluting Stent Implantation in Diabetic Patients—A Randomised Intravascular Ultrasound Study, The American Journal of Cardiology, Oct. 20-25, 2007, TCT Abstracts/Electronic, TCT 386.

Meredith et al., Clinical Outcomes at 1 Year for the Next-Generation Endeavor Resolute Stent: The RESOLUTE First-In-Human Study, The American Journal of Cardiology, Oct. 20-25, 2007, TCT Abstracts/Electronic, TCT 397.

Williams et al., Outcomes of 6906 Patients Undergoing Percutaneous Coronary Intervention in the Era of Drug-Eluting Stents: Report of the US DEScover Registry, Circulation, Nov. 14, 2006, pp. 1-9.

Rutherford et al., Substantial inhibition of neo-intimal response to balloon injury in the rat carotid artery using a combination of antibodies to platelet-derived growth factor-BB and basic fibroblast growth factor, Atherosclerosis, 1997, vol. 130, pp. 45-51.

Folkman et al., A Heparin-Binding Angiogenic Protein-Basic Fibroblast Growth Factor-Is Stored Within Basement Membrane, American Journal 400of Pathology, Feb. 1988, vol. 130 No. 2, pp. 393-400.

\* cited by examiner

DRUG-ELUTING CORONARY ARTERY STENT COATED WITH ANTI-PLATELET-DERIVED GROWTH FACTOR ANTIBODIES OVERLAYING EXTRACELLULAR MATRIX PROTEINS WITH AN OUTER COATING OF ANTI-INFLAMMATORY (CALCINEURIN INHIBITOR) AND/OR ANTI-PROLIFERATIVES

CROSS REFERENCE TO RELATED APPLICATION(S)

This application is a continuation-in-part and claims the benefit of priority under 35 U.S.C. §120 of U.S. patent application Ser. No. 11/972,540, filed Jan. 10, 2008 now abandoned, which is a utility and claims the benefit of priority under 35 U.S.C. §119(e) of U.S. Application Ser. No. 60/880,420, filed Jan. 11, 2007, and the benefit of priority under 35 USC §119(e) of U.S. Application Ser. No. 60/901,338, filed Feb. 13, 2007, and the benefit of priority under 35 U.S.C. §119(e) of U.S. Application Ser. No. 61/042,174, filed Apr. 3, 2008 and the benefit of priority under 35 USC §119(e) of U.S. Application Ser. No. 61/006,309, filed Jan. 3, 2008. The disclosure of each of the prior applications is considered part of and is incorporated by reference in the disclosure of this application.

BACKGROUND OF THE INVENTION

1. Field of the Invention

The invention relates generally to a vascular implant and, more specifically, to a multiple drug-eluting intravascular implant and methods of using the implant to perform percutaneous transluminal coronary angioplasty and intracerebral vessel repair at target lesions for the treatment of heart disease and cerebrovascular pathology associated with vascular occlusions.

2. Background Information

Percutaneous transluminal coronary angioplasty (PCTA) is a procedures which is well established for the treatment of blockages, lesions, stenosis, thrombus, and the like, which may be present in body lumens such as the coronary arteries and other vessels.

A widely used form of percutaneous coronary angioplasty makes use of a dilation balloon catheter which is introduced into and advanced through a lumen or body vessel until the distal end thereof is at a desired location in the vasculature. Once in position across an afflicted site, the expandable portion of the catheter, or balloon, is inflated to a predetermined size with a fluid at relatively high pressures. By doing so, the vessel is dilated, thereby radially compressing the atherosclerotic plaque of any lesion present against the inside of the artery wall, and/or otherwise treating the afflicted area of the vessel. The balloon is then deflated to a small profile so that the dilation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Stents, grafts, stent-grafts, vena cava filters and similar implantable medical devices, collectively referred to as stents, are radially expandable endoprostheses which are typically intravascular implants capable of being implanted and enlarged radially after being introduced. Stents may be implanted in a variety of body lumens or vessels such as within the vascular system, urinary tracts, bile ducts, and the like. Stents may be used to reinforce body vessels and to prevent restenosis following angioplasty in the vascular system. They may be self-expanding, such as a nitinol shape memory stent, mechanically expandable, such as a balloon expandable stent, or hybrid expandable.

Pharmaceutical compounds may be coated directly on the stent to provide an efficacious point-of-use drug delivery system. Such systems can be used to prevent insertion induced complications that may include inflammation, infections, thrombosis or blood clots, restenosis, and proliferation of cell growth, where such growth may occlude passageways.

One approach has been to coat the stents with various anti-thrombotic or anti-restenotic agents in order to reduce thrombosis and restenosis. For example, impregnating stents with radioactive material appears to inhibit restenosis by inhibiting migration and proliferation of myofibroblasts. Irradiation of the treated vessel can pose safety problems for the physician and the patient. In addition, irradiation does not permit uniform treatment of the affected vessel.

Alternatively, stents have also been coated with chemical agents such as heparin or phosphorylcholine, both of which appear to decrease thrombosis and restenosis. Although heparin and phosphorylcholine appear to markedly reduce restenosis in animal models in the short term, treatment with these agents appears to have no long-term effect on preventing restenosis. It is not feasible to load stents with sufficient therapeutically effective quantities of either heparin or phosphorylcholine to make treatment of restenosis in this manner practical.

Synthetic grafts have been treated in a variety of ways to reduce postoperative restenosis and thrombosis. For example, composites of polyurethane such as meshed polycarbonate urethane have been reported to reduce restenosis as compared with expanded polytetrafluoroethylene (ePTFE) grafts. The surface of the graft has also been modified using radiofrequency glow discharge to add polyterephalate to the ePTFE graft. Synthetic grafts have also been impregnated with biomolecules such as collagen. However, none of these approaches has significantly reduced the incidence of thrombosis or restenosis over an extended period of time.

Synthetic grafts have also been seeded with endothelial cells, but the clinical results with endothelial seeding have been generally poor, i.e., low post-operative patency rates. Further, although drug-eluting (DE) coronary artery stents have shown superior short- and mid-term results in lower rates of neovascularization compared to bare metal (BM) stents, long term (≥2 years) restenosis rates over 5-15% at 3 year post-procedure are still considerable due to "late thrombosis," and are not significantly better than BM stents in certain patient groups. For example, in diabetic patients, restenosis rates of DE stents are as high as 20-30%, and these rates are even higher for BM stents for this group.

The addition of a coating of anti-inflammatory or anti-proliferative drugs to BM stents has resulted in improved performance of these stents in their role to "prop-open" previously clogged arteries, compared to uncoated BM stents, in reducing the risk of early or mid-term re-blockage. However, patients with the most severe forms of atherosclerosis still have high rates of re-blockage after stent implantation, in spite of the use of DE stents.

SUMMARY OF THE INVENTION

The present invention relates to a combination of agents, including an anti-proliferative agent, an anti-inflammatory agent, an anti-growth factor, and an extracellular matrix (ECM) molecule or multiple types of ECM molecules coated on an implant to prevent acute thrombosis, promote in-growth of normal endothelial cells in the stent lining and/or suppress neovascularization, and thereby reduce restenosis rates for drug eluting implants, including stents. The present invention also relates to methods of using such multiple drug-eluting implants for the treatment of heart disease, cerebrovascular disorders, and other vascular conditions.

In one embodiment, a vascular implant is disclosed including a first outer layer coating including an anti-proliferative agent and an anti-inflammatory agent, a second middle layer coating including at least one anti-growth factor agent, and a third bottom layer coating including at least one non-thrombogenic extracellular matrix (ntECM) molecule, where the first outer layer coating is formulated for immediate and sustained release of the anti-proliferative agent and the anti-inflammatory agent upon implantation and the second middle layer coating is formulated for delayed sustained release of the at least one anti-growth factor agent, and where the at least one ntECM molecule is permanently affixed to the lumen or interstices of the implant.

In one aspect, the middle layer coating intercalates into the third bottom layer. In another aspect, the at least one anti-growth factor agent is covalently bound to one or more permanent surfaces of the implant.

In one aspect, the at least one anti-growth factor agent is covalently bound to one or more polymers coating the implant. In another aspect, the anti-proliferative agent includes, but is not limited to, paclitaxel and actinomycin, and the like. In a related aspect, the anti-proliferative agent is paclitaxel.

In another aspect, the anti-inflammatory agent includes, but is not limited to, calcineurin inhibitors such as sirolimus, tacrolimus, everolimus, zotarolimus, and the like. In a related aspect, the anti-inflammatory agent is sirolimus.

In one aspect, the at least one anti-growth agent includes, but is not limited to, an anti-platelet derived growth factor (PDGF) polyclonal or monoclonal antibody or a PDGF-binding fragment thereof, an anti-PDGF receptor (PDGFR) polyclonal or monoclonal antibody or a PDGFR-binding fragment thereof, an anti-basic fibroblast growth factor (bFGF) polyclonal or monoclonal antibody or a bFGF-binding fragment thereof, or anti-FGF receptor (FGFR) polyclonal or monoclonal antibody or an FGFR-binding fragment thereof, or a combination thereof. In a related aspect, the at least one anti-growth agent is an anti-PDGFR monoclonal antibody or a PDGFR-binding fragment thereof. In a further related aspect, the at least one anti-growth agent is an anti-bFGF or anti-FGFR monoclonal antibody or a bFGF-binding or an FGFR-binding fragment thereof.

In another aspect, the at least one ntECM molecule includes, but is not limited to, laminin, heparin, heparin sulfate proteoglycan, elastin, and fibronectin, chondroitin, or a combination thereof. In a related aspect, the at least one ntECM molecule is fibronectin. In one aspect, ntECM molecules enhance attachment and in-growth of normal endothelial cells into the stent lumen.

In one aspect, the implant is a tubular vascular implant. In a related aspect, the tubular vascular implant is a stent.

In another embodiment, a tubular vascular implant is disclosed including, a first outer layer coating including paclitaxel and sirolimus and a second middle layer coating including at least one anti-growth factor agent, where the first outer layer coating is formulated for immediate sustained release of the paclitaxel and sirolimus upon implantation and the second middle layer coating is formulated for delayed sustained release of the at least one anti-growth factor agent.

In a related aspect, the device further includes a third bottom layer coating including at least one non-thrombogenic extracellular matrix (ntECM) molecule, where the at least one ntECM molecule is permanently affixed to one or more surfaces of the implant.

In one embodiment, a method of preventing target lesion restenosis (TLR) or target vessel restenosis (TVR) in a subject with clogged arteries including inserting a tubular vascular implant is disclosed, where the implant includes: a first outer layer coating including an anti-proliferative agent and an anti-inflammatory agent, a second middle layer coating including at least one anti-growth factor agent, and a third bottom layer coating including at least one non-thrombogenic extracellular matrix molecule (ntECM), where the first outer layer coating is formulated for immediate sustained release of the anti-proliferative agent and the anti-inflammatory agent upon implantation and the second middle layer coating is formulated for delayed sustained release of the at least one anti-growth factor agent, and where the at least one ntECM molecule is permanently affixed to one or more surfaces of the implant.

In one aspect, the coatings may be on the outer surface, on the ends, or on one end of the implant. In another aspect, the method includes administration of an anticoagulant, where the anticoagulant includes, but is not limited to, antithrombin, protein C, thrombomodulin, heparin, coumarin, 1,3-indanedione, and warfarin.

DETAILED DESCRIPTION OF THE INVENTION

Figure 1:
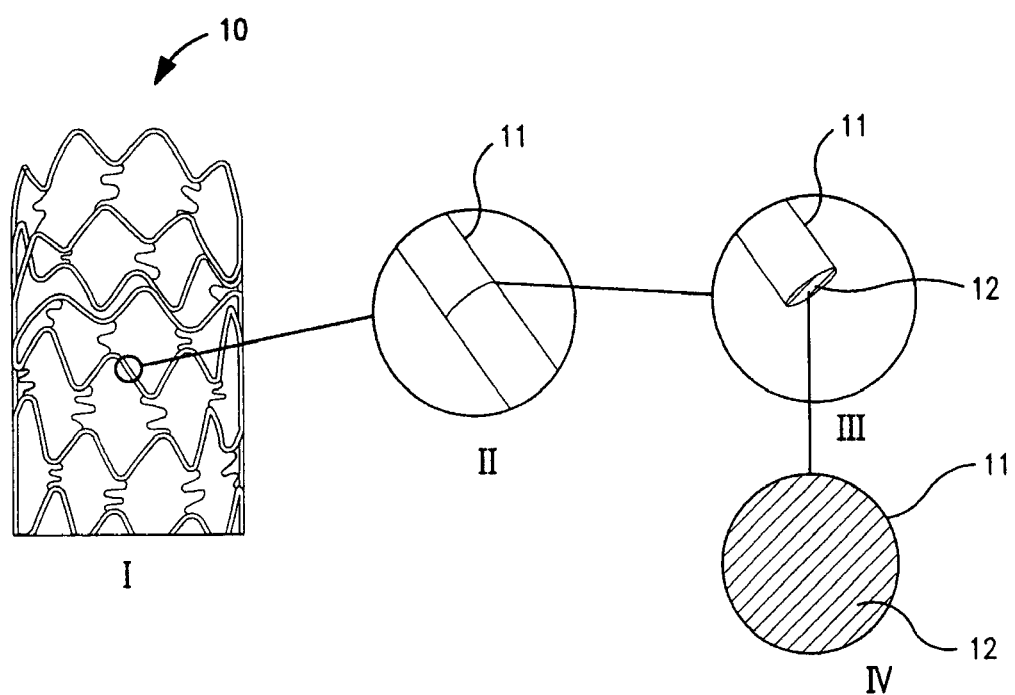
FIG. 1 shows (I) a perspective view of a bare metal stent, including illustrations of (II) a main wire strut of the stent meshwork, (III) a perspective view of the cross section of a main wire strut, and (IV) an end view of the main wire strut cross section.

Before the present composition, methods, and treatment methodology are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Drug-eluting (DE) coronary artery stents have shown superior short- and mid-term results in lower rates of neovascularization compared to bare metal (BM) stents, long term (≥2 years) restenosis rates over 5-15% at 3 year post-procedure are still considerable due to "late thrombosis."

The term "late thrombosis" means a stented vessel clogging at 2 to 3 years post implantation. The clog may be inside the stent (target lesion restenosis; TLR) or outside the stent (target vessel revascularization; TVR).

While not being bound by theory, "late thrombosis" for DE stents may be due to the presence of an "unnatural" polymer stent coating which seems to act as an irritant or an inflammatory stimulus, and thus, prevents in-growth of a normal endothelial lining onto the inside of the stented vessel. Other causes suggested include persistent inflammation around the stent due to vessel trauma via stent placement or simultaneous tissue damage at distal sites, where healing resources are consumed (e.g., but not limited to, major bleeding at catheter site or acute heart attack). Alternatively, the cause may be due to a lack of healing. In contrast, successful BM stents typically have a healthy lining of endothelium on the inner lumen of the stent.

For the present invention, a stent design is disclosed which includes one or more outer coatings having two anti-proliferative and anti-inflammatory agents (e.g., but not limited to Paclitaxel, or taxane, or a derivative thereof, which taxane or derivative possesses anti-proliferative activity and sirolimus, or calcineurin inhibitor, or derivative thereof, which calcineurin inhibitor or derivative possesses anti-inflammatory activity); one or more additional layers or coatings covalently or releasably bound to the stent including an anti-growth factor agent (e.g., but not limited to monoclonal antibody directed to platelet derived growth factor (PDGF), PDGF receptor (PDGFR), basic fibroblast growth factor (bFGF) or FGF receptor (FGFR) or a growth factor-binding fragment thereof); and one or more layers or coatings covalently or releasably bound to the lumenal surface or within the interstices of the stent, where coatings include non-thrombogenic "extracellular matrix" (ECM) molecules, and where the ECM molecules promote the attachment and in-growth of endothelial cells to the lumenal or interstices of the stent. In one aspect, such ECM molecules promote vessel healing by forming a scaffold for endothelial cell attachment. In a related aspect, ECM molecules include, but are not limited to, laminen, heparin sulfate proteoglycan, elastin, or a combination thereof. In another aspect, fibronectin is paired with individual ECM molecules or combinations of ECM molecules.

In general, the therapeutic agent (i.e., drug) for use in connection with the present invention can be any pharmaceutically acceptable therapeutic agent. As used herein "pharmaceutically acceptable" means that an agent that is approved or capable of being approved by the United States Food and Drug Administration or Department of Agriculture for use in humans or animals when incorporated in or on an implantable or insertable medical device. For example, therapeutic agents include, but are not limited to, anti-inflammatory agents, anti-growth agents, anti-proliferative agents, and combinations thereof.

Further, drugs useful for the present invention include, but are not limited to, anti-thrombogenic agents such as heparin, heparin sulfate proteoglycan, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; immunosuppressants such as sirolimus (RAPAMYCIN), tacrolimus, everolimus and dexamethasone, antineoplastic/antiproliferative/anti-miotic agents such as paclitaxel, 5-fluorouracil, cisplatin, vinblastine, vincristine, epothilones, methotrexate and other folate antagonists (e.g., pemetrxed), azathioprine, halofuginone, adriamycin, actinomycin and mutamycin; endostatin, angiostatin and thymidine kinase inhibitors, and its analogs or derivatives; anesthetic agents such as lidocaine, bupivacaine, and ropivacaine; anti-coagulants such as D-Phe-Pro-Arg chloromethyl ketone, an RGD peptide-containing compound, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides; vascular cell growth promotors such as growth factors, Vascular Endothelial Growth Factors (VEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, antibodies directed against PDGF, antibodies directed against PDGFR, antibodies directed against bFGF, antibodies against FGFR, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

The implants or stents of the present invention may be fabricated utilizing any number of methods. For example, the stent may be fabricated from a hollow or formed stainless steel tube or wire meshwork that may be machined using lasers, electric discharge milling, chemical etching or other means. The stent is inserted into the body and placed at the desired site in an unexpanded form. In one embodiment, expansion may be effected in a blood vessel by a balloon catheter, where the final diameter of the stent is a function of the diameter of the balloon catheter used.

It should be appreciated that a stent in accordance with the present invention may be embodied in a shape-memory material, including, for example, an appropriate alloy of nickel and titanium or stainless steel.

Structures formed from stainless steel may be made self-expanding by configuring the stainless steel in a predetermined manner, for example, by twisting it into a braided configuration. In this embodiment after the stent has been formed it may be compressed so as to occupy a space sufficiently small as to permit its insertion in a blood vessel or other tissue by insertion means, wherein the insertion means include a suitable catheter, or flexible rod.

On emerging from the catheter, the stent may be configured to expand into the desired configuration where the expansion is automatic or triggered by a change in pressure, temperature or electrical stimulation.

Regardless of the design of the stent, it is preferable to have the drug combination dosage applied with enough specificity and a sufficient concentration to provide an effective dosage in the prescribed area. In this regard, a "reservoir size" in the coating is preferably sized to adequately apply the drug combination dosage at the desired location and in the desired amount.

In one embodiment, the entire inner and outer surface of the stent may be coated with drug/drug combinations in therapeutic dosage amounts. It is, however, important to note that the coating techniques may vary depending on the drug combinations. Also, the coating techniques may vary depending on the material comprising the stent or other intraluminal medical device. In one aspect, the coatings may be on the outer surface, the ends, or one end of the implant.

The tubular vascular implant of the present invention comprises the immediate and/or delayed sustained release drug delivery coatings. The coating may be applied to the implant via a conventional coating process, such as impregnating coating, spray coating and dip coating.

In one embodiment, a tubular vascular implant of the invention includes an elongate radially expandable tubular implant having an interior luminal surface and an opposite exterior surface extending along a longitudinal implant axis. The implant may include a permanent implantable stent, an implantable grafted stent, or a temporary stent, where the temporary stent is defined as a stent that is expandable inside a vessel and is thereafter retractable from the vessel. The implant configuration may comprise a coil stent, a memory coil stent, a Nitinol stent, a mesh stent, a scaffold stent, a sleeve stent, a permeable stent, a stent having a temperature sensor, a porous stent, and the like. The implant may be deployed according to conventional methodology, such as by an inflatable balloon catheter, by a self-deployment mechanism (after release from a catheter), or by other appropriate means. The elongate radially expandable tubular implant may be a grafted stent, where the grafted stent is a composite device having a stent inside or outside of a graft. The graft may be a vascular graft, such as an ePTFE graft, a biological graft, or a woven graft. As appropriate, the subject drugs may be incorporated into the grafted material.

In one embodiment, a tubular vascular implant is disclosed including a first outer layer coating including an anti-proliferative agent and an anti-inflammatory agent, a second middle layer coating including at least one anti-growth factor agent, and a third bottom layer coating including at least one non-thrombogenic extracellular matrix (ntECM) molecule, where the first outer layer coating is formulated for immediate and sustained release of the anti-proliferative agent and the anti-inflammatory agent upon implantation and the second middle layer coating is formulated for delayed sustained release of the at least one anti-growth factor agent, and where the at least one ECM molecule is permanently affixed to one or more surfaces of the implant. As used herein, "non-thrombogenic" means reduced tendency of a material in contact with the blood to produce a thrombus, or clot, including emboli or activation of the immune pathway or complement system.

In one aspect, the ntECM may be applied to the stent as a plasma cryoprecipitate or as a synthetic fragment, where the fragment functions to attach endothelial cells and where the immunogenicity of the fragment is reduced relative to native or naturally occurring ntECM. In one aspect, an ntECM may be tethered to the stent by antibodies, diantibodies, or functional fragments thereof, directed to ntECM, where the antibodies capture the ntECM from circulating plasma. In a related aspect, the use of tethered ntECM may be combined with short term anticoagulant administration to ensure that thrombogenesis is reduced at the site of implantation. Such anticoagulants may include, but are not limited to, antithrombin, protein C, thrombomodulin, heparins, coumarins, 1,3-indanediones, and warfarin.

In another aspect, the ECM molecule is affixed to lumenal or interstitial surfaces of the stent. The term "interstitial," or grammatical variations thereof, means a small interval or space or gap in a structure.

The drug combinations may be incorporated onto or affixed to the implant in a number of ways. In one embodiment, the drug combination is directly incorporated into a polymeric matrix and sprayed onto the outer surface of the implant. The drug combination elutes from the polymeric matrix over time and enters the surrounding tissue. The drug combination preferably remains on the implant for at least three days up to approximately six months, and more preferably between seven and thirty days.

Any number of non-erodible polymers may be utilized in conjunction with the drug combination. Polymers that can be used for coatings in this application can be absorbable or non-absorbable and must be biocompatible to minimize irritation to the vessel wall. The polymer may be either biostable or bioabsorbable depending on the desired rate of release or the desired degree of polymer stability, but a bioabsorbable polymer is preferred since, unlike biostable polymer, it will not be present long after implantation to cause any adverse, chronic local response. Furthermore, bioabsorbable polymers do not present the risk that over extended periods of time there could be an adhesion loss between the implant and coating caused by the stresses of the biological environment that could dislodge the coating and introduce further problems even after the implant is encapsulated in tissue.

Suitable bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof. For the purpose of this invention aliphatic polyesters include homopolymers and copolymers of lactide (which includes lactic acid d-, l- and meso lactide), epsilon.-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-2-one and polymer blends thereof. Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in Journal of Biomaterials Research, Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and ε-caprolactone such as are described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182. Polyanhydrides from diacids of the form HOOC—$C_6H_4$—O—$(CH_2)_m$—O—$C_6H_4$—COOH where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213 and 5,700,583. Polyorthoesters such as those described by Heller in Handbook of Biodegradable Polymers, edited by Domb, Kost and Wisemen, Hardwood Academic Press, 1997, pages 99-118. Polymeric biomolecules for the purpose of this invention include naturally occurring materials that may be enzymatically degraded in the human body or are hydrolytically unstable in the human body such as fibrin, fibrinogen, collagen, elastin, and absorbable biocompatible polysaccharides such as chitosan, starch, fatty acids (and esters thereof), glucoso-glycans and hyaluronic acid.

Suitable biostable polymers with relatively low chronic tissue response, such as polyurethanes, silicones, poly(meth) acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the implant. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as ethylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitreate; cellulose propionate; cellulose ethers (i.e., carboxymethyl cellulose and hydroxyalkyl celluloses); and combinations thereof. Polyamides for the purpose of this application would also include polyamides of the form —NH—$(CH_2)_n$—CO— and NH—$(CH_2)_x$—NH—CO—$(CH_2)_y$—CO, wherein n is preferably an integer in from 6 to 13; x is an integer in the range of form 6 to 12; and y is an integer in the range of from 4 to 16. The list provided above is illustrative but not limiting.

In certain embodiments, the polymers used for coatings have molecular weights high enough as to not be waxy or tacky. The polymers preferably adhere to the stent and are readily deformable after deposition on the implant as to be able to be displaced by hemodynamic stresses. The polymers molecular weight be high enough to provide sufficient toughness so that the polymers will not to be rubbed off during handling or deployment of the implant and not crack during expansion of the implant, though cracking can be avoided by careful placement of the coating, e.g., on portions of the implant which do not change shape between expanded and collapsed forms. The melting point of the polymer used in the present invention should have a melting temperature above 40° C., preferably above about 45° C., more preferably above 50° C. and most preferably above 55° C.

Coating may be formulated by mixing one or more of the therapeutic agents with the coating polymers in a coating mixture. The therapeutic agent may be present as a liquid, a finely divided solid, or any other appropriate physical form. Optionally, the mixture may include one or more additives, e.g., nontoxic auxiliary substances such as diluents, carriers, excipients, stabilizers or the like. Other suitable additives may be formulated with the polymer and pharmaceutically active agent or compound. For example, hydrophilic polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxylmethyl cellulose, hydroxymethyl cellulose and combination thereof to an aliphatic polyester coating to modify the release profile. Appropriate relative amounts can be determined by monitoring the in vitro and/or in vivo release profiles for the therapeutic agents.

In one embodiment, which can be useful where the drugs are provided as individual monomers rather than as co-drugs, the polymeric matrix comprises multiple layers. A base layer may comprise a solution of poly(ethylene-covinylacetate) and polybutylmethacrylate. The drug combination may be incorporated into this base layer. Another layer may comprise only polybutylmethacrylate and acts as a diffusion barrier to prevent the drug combination from eluting too quickly. The thickness of the layer or coat determines the rate at which the drug combination elutes from the matrix. Essentially, the drug combination elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the implant. For example, acid cleaning, alkaline (base) cleaning, salinization and parylene deposition may be used as part of the overall process.

To further illustrate, a poly(ethylene-co-vinylacetate), polybutylmethacrylate and drug combination solution, for example, may be incorporated into or onto the implant in a number of ways. For example, the solution may be sprayed onto the implant or the implant may be dipped into the solution. Other methods include spin coating and RF plasma polymerization. In one embodiment, the solution is sprayed onto the implant and then allowed to dry. In another embodiment, the solution may be electrically charged to one polarity and the implant electrically changed to the opposite polarity.

In this manner, the solution and implant will be attracted to one another. In using this type of spraying process, waste may be reduced and more precise control over the thickness of the coat may be achieved.

In another embodiment, the drug combination or other therapeutic agents may be incorporated into a polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, where the relative amounts of the first moiety and the second moiety are effective to provide the coating and film produced therefrom with properties effective for use in treating implantable devices.

In one embodiment according to the present invention, the exterior surface of the expandable tubular implant of the present invention comprises a coating according to the present invention. The exterior surface of an implant having a coating is the tissue-contacting surface and is biocompatible. The "immediate or delayed sustained release drug delivery system coated surface" is synonymous with "coated surface," which surface is coated, covered or impregnated with immediate and delayed sustained release drug delivery system according to the present invention.

In another embodiment, the interior luminal surface or entire surface (i.e., both interior and exterior surfaces) of an elongate radially expandable tubular implant of the present invention has the coated surface. The interior luminal surface having the sustained release drug delivery system coating may also be the fluid contacting surface, and is biocompatible and blood compatible.

In certain embodiments, the implant, such as a stent, may be coated with a non-polymeric coating, preferably a porous coating, that includes (e.g., is impregnated with, or is admixed with) one or more pharmaceutically active compounds. Such coatings may include ceramic materials, organic materials substantially insoluble in physiologic fluids, and other suitable coatings, as will be understood by those of skill in the art. In certain other embodiments, the surface of the device itself is porous, e.g., the device may be formed of a porous material such as a ceramic or specially fabricated polymeric material, or the device may be formed in such a way that the surface achieves a porous character, and the pharmaceutically active compound is carried in the pores of the device's surface, thereby permitting gradual release of the compound upon introduction into a biological environment. The surface of the device may further be coated with a polymeric material, e.g., that modulates the release of the agent(s), that improves biocompatibility, or otherwise improves the performance of the device in the medical treatment.

Another aspect of the invention relates to an implant having a matrix, such as a fibrous matrix, such as a woven or non-woven cloth, e.g., vascular gauze (such as a GORTEX™ gauze), in which one or more pharmaceutically active compounds are disposed. In certain embodiments, the matrix is disposed on a implant, either wrapped around individual elements (e.g., wires) of the frame, or enveloping the entire device.

U.S. Pat. Nos. 5,773,019, 6,001,386, and 6,051,576 disclose implantable controlled-release devices and drugs. The inventive process for making a surface coated implants includes deposition onto the implant of a coating by, for example, dip coating or spray coating. In the case of coating one or both ends of the implant, only the surface to be coated is exposed to the dip or spray. The treated surface may be all or part of an interior luminal surface, an exterior surface, or both interior and exterior surfaces of the implant. The implant may be made of a porous material to enhance deposition or coating into a plurality of micropores on or in the applicable implant surface, wherein the microporous size is preferably about 100 microns or less.

Problems associated with treating restinosis and neointimal hyperplasia can be addressed by the choice of pharmaceutical agent used to coat the implant. In certain embodiments of the present invention, the chosen pharmaceutical agent is a moiety of low solubility and comprises at least four pharmaceutically active compounds. The pharmaceutically active compounds can be the same or different chemical species, and can be formed, as desired, in equimolar or non-equimolar concentrations to provide optimal treatment based on the relative activities and other pharmaco-kinetic properties of the compounds. The drug combination, particularly where co-drug formulations are used, may itself be advantageously relatively insoluble in physiologic fluids, such as blood and blood plasma, and has the property of regenerating any or all of the pharmaceutically active compounds when dissolved in physiologic fluids. In other words, to the extent that the low-solubility agent dissolves in physiologic fluids, it is quickly and efficiently converted into the constituent pharmaceutically active compounds upon dissolution. The low-solubility of the pharmaceutical agent thus insures persistence of the agent in the vicinity of the prescribed region. The quick conversion of the low-solubility pharmaceutical agent into the constituent pharmaceutically active compounds insures a steady, controlled, dose of the pharmaceutically active compounds near the site to be treated.

In some embodiments according to the present invention, the pharmaceutically active compounds are covalently bonded directly to one another. Where pharmaceutically active compounds are directly bonded to one another by a covalent bond, the bond may be formed by forming a suitable covalent linkage through an active group on each active compound. For instance, an acid group on one pharmaceutically active compound may be condensed with an amine, an acid or an alcohol on another pharmaceutically active compound to form the corresponding amide, anhydride or ester, respectively.

In addition to carboxylic acid groups, amine groups, and hydroxyl groups, other suitable active groups for forming linkages between pharmaceutically active moieties include sulfonyl groups, sulthydryl groups, and the haloic acid and acid anhydride derivatives of carboxylic acids.

In other embodiments, the pharmaceutically active compounds may be covalently linked to one another through an intermediate linker. The linker advantageously possesses two active groups, one of which is complementary to an active group on one pharmaceutically active compound, and the other of which is complementary to an active group on the other pharmaceutically active compound. For example, where the pharmaceutically active compounds both possess free hydroxyl groups, the linker may suitably be a di-acid, which will react with both compounds to form a diether linkage between the two residues. In addition to carboxylic acid groups, amine groups, and hydroxyl groups, other suitable active groups for forming linkages between pharmaceutically active moieties include sulfonyl groups, sulfhydryl groups, and the haloic acid and acid anhydride derivatives of carboxylic acids.

Suitable di-acid linkers include oxalic, malonic, succinic, glutaric, adipic, pimelic, suberic, azelaic, sebacic, maleic, fumaric, tartaric, phthalic, isophthalic, and terephthalic acids.

While di-acids are named, the skilled artisan will recognize that in certain circumstances the corresponding acid halides or acid anhydrides (either unilateral or bilateral) are preferred as linker reagents. A preferred anhydride is succinic anhydride. Another preferred anhydride is maleic anhydride. Other anhydrides and/or acid halides may be employed by the skilled artisan to good effect.

Suitable amino acids include β-butyric acid, 2-aminoacetic acid, 3-aminopropanoic acid, 4-aminobutanoic acid, 5-aminopentanoic acid, 6-aminohexanoic acid, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine. Again, the acid group of the suitable amino acids may be converted to the anhydride or acid halide form prior to their use as linker groups.

Suitable diamines include 1,2-diaminoethane, 1,3-diaminopropane, 1,4-diaminobutane, 1,5-diaminopentane, 1,6-diaminohexane.

Suitable aminoalcohols include 2-hydroxy-1-aminoethane, 3-hydroxy-1-aminoethane, 4-hydroxy-1-aminobutane, 5-hydroxy-1-aminopentane, 6-hydroxy-1-aminohexane.

Suitable hydroxyalkyl acids include 2-hydroxyacetic acid, 3-hydroxypropanoic acid, 4-hydroxybutanoic acid, 5-hydroxypentanoic acid, 5-hydroxyhexanoic acid.

The skilled artisan will recognize that by selecting pharmaceutical moieties having suitable active groups, and by matching them to suitable linkers, a broad palette of inventive compounds may be prepared within the scope of the present invention.

As used in regard to the low-solubility pharmaceutical agent, the term "low-solubility" relates to the solubility of the pharmaceutical agent in biological fluids, such as blood plasma, lymphatic fluid, peritoneal fluid, and the like. In general, "low-solubility" means that the pharmaceutical agent is only very slightly soluble in aqueous solutions having pH in the range of about 5 to about 8, and in particular to physiologic solutions, such as blood, blood plasma, and the like. Some low-solubility agents according to the present invention will have solubilities of less than about 100 μg/ml, preferably less than about 20 μg/ml, more preferably less than about 15 μg/ml, and more preferably, less than about 10 μg/ml. Solubility is in water at a temperature of 25° C. as measured by the procedures set forth in the 1995 USP, unless otherwise stated. This includes compounds which are slightly soluble (about 10 mg/ml to about 1 mg/ml), very slightly soluble (about 1 mg/ml to about 0.1 mg/ml) and practically insoluble or insoluble compounds (less than about 0.1 mg/ml).

Compounds of the present invention are slowly dissolved in physiologic fluids, but are relatively quickly dissociated into pharmaceutically active compounds upon dissolution in physiologic fluids. In some embodiments the dissolution rate of the inventive compounds is in the range of about 0.001 μg/day to about 10 μg/day. In certain embodiments, the compounds have dissolution rates in the range of about 0.01 to about 1 μg/day. In other embodiments, the inventive compounds have dissolution rates of about 0.1 μg/day.

The use of polymeric matrices to modulate the release of bioactive agents and their bioavailability in many controlled release systems allows maximization of the efficiency and a prolonging of the pharmacological effects of many drugs while minimizing, or eliminating, any potential toxicity that may be associated with single-dose administration. Among the major factors that control the release of a drug from a polymeric matrix are its molecular size (or molecular weight) and water solubility. The use of a pseudodimer of a bioactive agent may be useful to control release. This approach increases drug size and decreases its solubility, without compromising its timely bioavailability in its active, free form. The molecular weight of the pseudodimeric conjugated drug may be between 200 and 60,000 Da, or larger.

A pseudodimer may be formed by two drug monomers by linking them at a non-pharmacologically significant point with a linking group. Formation of a pseudodimer of a drug increases the effective molecular weight of the drug without impacting its pharmacological moiety or bioavailability. In general, increasing the molecular weight decreases the water solubility of the bioactive agent. Increases in the molecular weight and decreases in water solubility provide mechanisms for delaying the elution of the modulated drug from the implant coating. Dispersion of the pseudodimeric conjugated drug throughout a polymeric matrix within the polymeric coating provides another mechanism for controlled release, as a larger molecular weight conjugated drug will generally exhibit slower diffusion from the coating.

In some embodiments according to the present invention, the pharmaceutical agent is dissolved within the polymer coating. In one aspect, it is preferred that the polymer coating be a relatively non-polar or hydrophobic polymer which acts as a good solvent for the relatively hydrophobic pharmaceutical agent. In another aspect, the pharmaceutical agent in the polymer coating should be such that the agent will dissolve thoroughly in the polymer coating, being distributed homogeneously throughout the polymer coating.

In some embodiments according to the present invention, the polymer is non-bioerodible. Examples of non-bioerodible polymers useful in the present invention include poly(ethylene-co-vinyl acetate) (EVA), polyvinylalcohol and polyurethanes, such as polycarbonate-based polyurethanes. In other embodiments of the present invention, the polymer is bioerodible. Examples of bioerodible polymers useful in the present invention include polyanhydride, polylactic acid, polyglycolic acid, polyorthoester, polyalkylcyanoacrylate or derivatives and copolymers thereof. The skilled artisan will recognize that the choice of bioerodibility or non-bioerodibility of the polymer depends upon the final physical form of the system. Other exemplary polymers include polysilicone and polymers derivatives from hyaluronic acid.

Moreover, suitable polymers include naturally occurring (collagen, hyaluronic acid) or synthetic materials that are biologically compatible with bodily fluids and mammalian tissues, and essentially insoluble in bodily fluids with which the polymer will come in contact. Other suitable polymers include polypropylene, polyester, polyethylene vinyl acetate (EVA), polyethylene oxide (PEO), polypropylene oxide, polycarboxylic acids, polyalkylacrylates, cellulose ethers, polyalkyl-alkyacrylate copolymers, polyester-polyurethane block copolymers, polyether-polyurethane block copolymers, polydioxanone, poly-(β-hydroxybutyrate), polylactic acid (PLA), polycaprolactone, polyglycolic acid, and PEO-PLA copolymers.

The coating of the present invention may be formed by mixing one or more suitable monomers and pharmaceutical agents, then polymerizing the monomer to form the polymer system. In this way, the agents are dissolved or dispersed in the polymer. In other embodiments, the agents are mixed into a liquid polymer or polymer dispersion and then the polymer is further processed to form the coating. Suitable further processing includes crosslinking with suitable crosslinking agents, further polymerization of the liquid polymer or polymer dispersion, copolymerization with a suitable monomer, block copolymerization with suitable polymer blocks, and the like. The further processing traps the drugs in the polymer so that the drugs are suspended or dispersed in the polymer coating.

In some embodiments according to the present invention, monomers for forming a polymer are combined with the pharmaceutically active agents and are mixed to make a homogeneous dispersion of the agents in the monomer solution. The dispersion is then applied to an implant according to a conventional coating process, after which the crosslinking process is initiated by a conventional initiator, such as UV light. In other embodiments according to the present invention, a polymer composition is combined with the pharmaceutically active agents to form a dispersion. The dispersion is then applied to an implant and the polymer is cross-linked to form a solid coating. In other embodiments according to the present invention, a polymer and the pharmaceutically active agents are combined with a suitable solvent to form a dispersion, which is then applied to an implant in a conventional fashion. The solvent is then removed by a conventional process, such as heat evaporation, with the result that the polymer and pharmaceutically active agents (together forming a sustained-release drug delivery system) remain on the implant as a coating.

An analogous process may be used where the pharmaceutically active agents are dissolved in the polymer composition.

In some embodiments according to the invention, the system comprises a polymer that is relatively rigid. In other embodiments, the system comprises a polymer that is soft and malleable. In still other embodiments, the system includes a polymer that has an adhesive character. Hardness, elasticity, adhesive, and other characteristics of the polymer may be varied as necessary.

In some embodiments according to the present invention, the polymer is non-bioerodible, or is bioerodible only at a rate slower than a dissolution rate of the pharmaceutical agents, and the diameter of the granules is such that when the coating is applied to the implant, the granules' surfaces are exposed to the ambient tissue. In such embodiments, dissolution of the pharmaceutical agents is proportional to the exposed surface area of the granules.

In other embodiments according to the present invention, the polymer coating is permeable to water in the surrounding tissue, e.g. in blood plasma. In such cases, water solution may permeate the polymer, thereby contacting the pharmaceutical agents. The rate of dissolution may be governed by a complex set of variables, such as the polymer's permeability, the solubility of the pharmaceutical agents, the pH, ionic strength, and protein composition, etc. of the physiologic fluid. In certain embodiments, however the permeability may be adjusted so that the rate of dissolution is governed primarily, or in some cases practically entirely, by the solubility of the pharmaceutical agents in the ambient liquid phase. In still other embodiments the pharmaceutical agents may have a high solubility in the surrounding fluid. In such cases the matrix permeability may be adjusted so that the rate of dissolution is governed primarily, or in some cases practically entirely, by the permeability of the polymer.

A coating for an implant, such as a stent, according to one embodiment of the present invention, can include a drug-polymer layer (also referred to as "reservoir" or "reservoir layer") or alternatively a polymer free drug layer, an optional primer layer and an optional topcoat layer. The drug-polymer layer serves as a reservoir for the drug. The reservoir layer or the polymer free drug layer can be applied directly onto the implant surface. The optional topcoat layer, which can be essentially free from any drugs, serves as a rate limiting membrane which helps to control the rate of release of the drug(s). The optional primer layer can be applied on the implant surface to improve the adhesion of the drug-polymer layer or the polymer free drug layer to the implant.

A control agent may be selected to provide a desired elution rate of the bioactive agent. Conjugated drugs may be synthesized such that a particular bioactive agent may have two different elution rates by selecting different control agents. A bioactive agent with two different elution rates, for example, would allow rapid delivery of the pharmacologically active drug within twenty-four hours of surgery, with a slower, steady delivery of the drug, for example, over the next six to twelve months.

The control agent may be covalently linked to the bioactive agent. Modulating the physical properties and bioavailability of bioactive agents without altering their pharmacological effects using covalent linking of the bioactive agents may include the use of polyethylene glycol (PEG) as the polymer. PEG may be linked covalently to complex proteins and other biomolecules to increase their biostability and, hence, increase their in vivo residence time. Linking the PEG to the bioactive agent, in practically all cases, has been achieved through the establishment of an ester linkage with the premise that the water-soluble PEG will be released by hydrolysis as the modified drug is metabolized.

The reservoir layer and the optional primer and topcoat layers of the coating can be formed on the implant by dissolving a polymer or a blend of polymers in a solvent, or a mixture of solvents, and applying the resulting polymer solution on the implant by spraying or immersing the implant in the solution. To incorporate a drug(s) into the reservoir layer, the drug(s) in a form of a solution can be combined with the polymer solution. Alternatively, to fabricate a polymer free drug layer, the drug(s) can be dissolved in a suitable solvent or mixture of solvents, and the resulting drug solution can be applied on the implant by spraying or immersing the implant in the drug solution.

Instead of introducing the drugs in a solution, the drugs can be introduced as a colloid system, such as a suspension in an appropriate solvent phase. To make the suspension, the drugs can be dispersed in the solvent phase using conventional techniques used in colloid chemistry. Depending on a variety of factors, e.g., the nature of the drugs, those having ordinary skill in the art will select the suitable solvent to form the solvent phase of the suspension, as well as the quantity of the drugs to be dispersed in the solvent phase. The suspension can be mixed with a polymer solution and the mixture can be applied on the implant as described above. Alternatively, the drug suspension can be applied on the implant without being mixed with the polymer solution.

The outermost layer of the implant coating may be either the topcoat layer or the reservoir layer (if the optional topcoat layer is not used). The outermost layer of the implant coating may be comprised of a blend of polymers, the blend to include one or more hydrophilic polymers and one or more hydrophobic polymers. The mass ratio between the hydrophilic and hydrophobic polymers in the outermost layer of the coating may be typically between about 1:100 and 1:9.

Generally, hydrophobicity of a polymer can be gauged using the Hildebrand solubility parameter, $\delta$. The term "Hildebrand solubility parameter" refers to a parameter measuring the cohesion of a substance. The $\delta$ parameter is determined as follows: $\delta = (\delta E/V)^{1/2}$ where $\delta$ is the solubility parameter, $(cal/cm^3)^{1/2}$; $\delta E$ is the energy of vaporization, cal/mole; and V is the molar volume, $cm^3/mole$.

Whichever polymer in the polymer blend has lower $\delta$ value compared to the $\delta$ value of the other polymer in the blend is designated as a hydrophobic polymer, and the polymer with higher δ value is designated as hydrophilic. If more than two polymers are used in the blend, then each can be ranked in order of its δ value. For the practice of the present invention, the value of δ of a particular polymer is inconsequential for classifying a polymer as hydrophobic or hydrophilic so long as the difference in the δ values of the two polymers is sufficient to allow the hydrophilic polymer to migrate or bloom to the surface.

Poly(ethylene-co-vinyl alcohol) (EVAL) is one example of a typical polymer that can be utilized as a hydrophobic component of the polymer blend used to fabricate the reservoir layer or the topcoat layer. EVAL can be used to make the optional primer layer as well. EVAL is a product of hydrolysis of ethylene-vinyl acetate copolymers and has the general formula $-[CH_2-CH_2]_m-[CH_2-CH(OH)]_n-$. EVAL may also include a terpolymer having up to about 5 molar % of units derived from styrene, propylene and other suitable unsaturated monomers. A brand of copolymer of ethylene and vinyl alcohol distributed commercially under the trade name EVAL by Aldrich Chemical Co. of Milwaukee, Wis., may be used.

Other examples of hydrophobic polymers and hydrophilic that can be used include polyacrylates, such as poly(butyl methacrylate), poly(ethyl methacrylate), and poly(ethyl methacrylate-co-butyl methacrylate), and fluorinated polymers and/or copolymers, such as poly(vinylidene fluoride) and poly(vinylidene fluoride-co-hexafluoro propene), poly(vinyl pyrrolidone), poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), co-poly(ether-esters), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Representative examples of some solvents suitable for making the implant coatings include N,N-dimethylacetamide (DMAC), N,N-dimethylformamide (DMF), tetrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., a 50:50 by mass mixture);
(2) water, i-propanol, and DMAC (e.g., a 10:3:87 by mass mixture);
(3) i-propanol and DMAC (e.g., 80:20, 50:50, or 20:80 by mass mixtures);
(4) acetone and cyclohexanone (e.g., 80:20, 50:50, or 20:80 by mass mixtures);
(5) acetone and xylene (e.g. a 50:50 by mass mixture);
(6) acetone, FLUX REMOVER AMS, and xylene (e.g., a 10:50:40 by mass mixture); and
(7) 1,1,2-trichloroethane and chloroform (e.g., a 80:20 by mass mixture).

FLUX REMOVER AMS is trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

Following the formation of the outermost layer of the implant coating comprising a blend of hydrophobic and hydrophilic polymer(s), the surface of the coating can be treated to enrich the surface with hydrophilic polymer(s). In order to enrich the surface with hydrophilic polymer(s), various methods of treatment of the implant coating can be used. According to one method of the post-coating treatment, the coated implant can be exposed to the environment of a humidifying chamber. The length of such treatment can be between about 12 hours and 28 hours, for example, about 24 hours, at a temperature of between about 40° C. and about 80° C., more narrowly, between about 45° C. and about 60° C., for example, about 50° C. and relative humidity of between about 90% and about 100%. Any commercially available humidifying chamber can be used. As a result of the exposure of the implant to high humidity levels at elevated temperatures, water is expected to be deposited on the surface of the implant coating. Water will gradually extract the hydrophilic polymer to the coating surface leading to migration of the hydrophilic polymer and its blooming to the coating-air interface.

According to another method of the post-coating treatment, the coated implant can be physically placed on a film of a hydrogel, for example, a poly(vinyl alcohol) hydrogel, and gently rolled back and forth a number of times covering the entire circumference of the implant. For example, the coated implant can be rolled in the described fashion between 5 and 10 times, while a pressure of between about 1 atm and 3 atm is applied to the implant when it is being rolled. The physical contact between the film of the hydrogel and the implant coating can alter the coating-air interface, resulting in extraction of the hydrophilic polymer and its blooming to the coating-air interface.

According to yet another method of the post-coating treatment, the coated implant can be cooled at a temperature between about 4° C. and about −20° C. for a period of time between about 30 minutes and about 2 hours. Following the cooling process, the implant can be either exposed to ambient air for about 24 hours, or treated in the humidifying chamber as described above. This procedure is expected to lead to condensation of water on the surface of the coating, resulting in extraction of the hydrophilic polymer and its blooming to the coating-air interface.

Optionally, any combination of the three methods of the post-coating treatment described above can be used, if desired. As another option, following the post-coating treatment, the coated implant can be heated to a temperature which is about equal to the glass transition temperature ($T_g$) of the hydrophobic component of the coating.

In another embodiment, instead of a blend of a hydrophobic and hydrophilic polymer, an interpenetrating polymer network (IPN) can be used to make the outermost layer of the implant coating, the IPN includes at least one hydrophobic component and at least one hydrophilic component. For the purposes of the present invention, the definition of the IPN used by the International Union of Pure and Applied Chemistry (IUPAC) is adopted. The IUPAC describes the IPN as a polymer comprising two or more networks which are at least partially interlaced on a molecular scale, to form both chemical and physical bonds between the networks. The networks of an IPN cannot be separated unless chemical bonds are broken. In other words, an IPN structure represents two or more polymer networks that are partially chemically cross-linked and partially physically entangled. One example of an IPN that can be used is a surface hydrogel.

One example of a product that can be used for forming the IPN is a PEG-based unsaturated product, for example, prepolymer of PEG-acrylate or PEG-methacrylate having a general formula $CH_2=CX-COO-[CH_2-CH_2-O]_n-H$, where X is hydrogen (acrylates) or methyl (methacrylates). The molecular weight of PEG-acrylate or methacrylate can be within a range of about 10,000 to 100,00 Daltons. PEG-acrylate or PEG-methacrylate prepolymer can be applied on the surface of the drug-polymer layer or topcoat layer and cured, for example, using a radical initiator which is activated by UV radiation (UV initiators), light (light initiators), or heat (thermal initiators). Examples of appropriate initiators include acetophenone, 2,2-dimethoxy-2-phenol-acetophenone (UV initiators), camproquinone, ethyl-4-N,N,-dimethyl aminobenzoate (light initiators), and benzoyl peroxide (thermal initiator). As a result of the curing process, PEG-acrylate or PEG-methacrylate will partially cross-link and partially physically entangle with the polymer of the underlying drug-polymer layer thus forming the outermost coat layer which includes an IPN. PEG-acrylate or PEG-methacrylate is intended to broadly include poly(ethylene glycol)-diacrylate (PEG-diacrylate) and poly(ethylene glycol)-dimethacrylate (PEG-dimethacrylate). PEG-acrylate or PEG-methacrylate and PEG-diacrylate or PEG-dimethacrylate can be optionally terminated, for example, with stearic acid, to form PEG-acrylate-stearate or PEG-methacrylate-stearate, respectively.

Examples of other products that can be used for forming the IPN include such unsaturated reactive products as N-vinylpyrrolidone, heparin and its derivatives, hyaluronic acid and its derivatives, some hydrogel-forming products such as poly(butyleneterephthalate-co-ethylene glycol) (PBT-PEG), and mixtures of any of these products with each other or with PEG-acrylate or PEG-methacrylate. A type of PBT-PEG polymers is also known under a trade name POLYACTIVE and is available from IsoTis Corp. of Holland.

After the IPN-based outermost coating has been formed, it can be subjected to a post-coating treatment to cause blooming or migration of the hydrophilic component of the IPN to the coating-air interface. For example, any method of the post-coating treatment described above, or any combination thereof, can be used.

One kind of an IPN is a hydrogel. If it is desirable to include a hydrogel in the outermost layer of the implant coating, PBT-PEG can be used as a hydrogel-forming product. PBT-PEG can be utilized for fabricating not only the outermost layer (e.g., the topcoat layer) of the coating but for making all other layers of the implant-coating (e.g., the middle layer or the bottom layer) as well.

Examples of the implants that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the implant can be of virtually any design. The implant can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Various embodiments of stent patterns for polymeric stents are disclosed herein. Stents may be composed partially or completely of polymers. In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body.

In addition, a implant of the present invention may be fabricated by coating the surface of the implant with an antibody. As used herein, the term "antibody" refers to one type of monoclonal or polyclonal antibody, where the monoclonal or polyclonal antibody binds to one antigen or a functional equivalent of that antigen. The term antibody encompasses any fragment of an antibody such as Fab, F(ab')$_2$ or Fc fragments.

As used herein, a "therapeutically effective amount of the antibody" means the amount of an antibody that binds to a growth factor (e.g., anti-VEGF or anti-PDGF) in order to effectively suppress the growth of myo-fibroblasts and smooth muscle cells inside the lumens of a stented artery or vessel, in the absence of interference of normal in-growth of endothelial cells. The amount of an antibody needed to practice the claimed invention varies with the nature of the antibody used. For example, the amount of an antibody used will depend on the binding constant between the antibody and the antigen against which it reacts. It is well known to those of ordinary skill in the art how to determine therapeutically effective amounts of an antibody to use with a particular antigen.

As used herein, "implant" refers to a device that is introduced temporarily or permanently into a mammal for the prophylaxis or therapy of a medical condition. These devices include any that are introduced subcutaneously, percutaneously or surgically to rest within an organ, tissue or lumen. Implants may include, stents, covered stents such as those covered with PTFE, or ePTFE, synthetic grafts, artificial heart valves, artificial hearts and fixtures to connect the prosthetic organ to the vascular circulation, venous valves, abdominal aortic aneurysm (AAA) grafts, inferior vena cava filters, permanent drug infusion catheters, embolic coils, embolic materials used in vascular embolization (e.g., PVA foams), and vascular sutures.

As used herein, "restenosis" refers to the accumulation of a layer of smooth muscle cells and matrix protein in the intima of an arterial wall. Vessels may become obstructed because of restenosis. After PTCA or PTA, smooth muscle cells from the media and adventitia, which are not normally present in the intima, proliferate and migrate to the intima and secrete proteins, forming an accumulation of smooth muscle cells and matrix protein within the intima. This accumulation causes a narrowing of the lumen of the artery, reducing blood flow distal to the narrowing. As used herein, "inhibition of restenosis" refers to the inhibition of migration and proliferation of smooth muscle cells accompanied by prevention of protein secretion so as to prevent restenosis and the complications arising therefrom.

The subjects that can be treated using the methods and compositions of this invention may be a mammal, or more specifically, a human, dog, cat, pig, rodent or monkey.

The methods of the present invention may be practiced in vivo or in vitro.

The term "endothelial cell" refers to endothelial cells at any developmental stage, from progenitor to mature. Fully differentiated endothelial cells may be isolated from an artery or vein such as a human umbilical vein, while progenitor endothelial cells are isolated from peripheral blood or bone marrow. The endothelial cells are bound to the medical devices by incubation of the endothelial cells with a medical device coated with a matrix that incorporates an antibody or other agent (e.g., ECM molecules) that is known to adhere to endothelial cells.

The methods of this invention may be practiced on any artery or vein. Included within the scope of this invention is atherosclerosis of any artery including coronary, intracerebral, infrainguinal, aortoiliac, subclavian, mesenteric and renal arteries. Other types of vessel obstructions, such as those resulting from a dissecting aneurysm are also encompassed by the invention.

The implant may be coated with endothelial cells after insertion into a vessel. Alternatively, the medical device is coated with the endothelial cells before insertion of the medical device. In either case, the presence of endothelial cells on the lumenal surface of the medical device inhibits or prevents restenosis and thrombosis.

Monoclonal antibodies useful in the method of the invention may be produced according to the standard techniques of Kohler and Milstein (Nature 265:495 497, 1975).

Also included within the scope of the invention are useful binding fragments of monoclonal antibodies such as the Fab, F(ab')$_2$, Fc fragments of these monoclonal antibodies, Fv fragments, diabodies, linear antibodies (Zapata et al., Protein Eng. 8(10): 1057-1062 [1995]), single-chain antibody molecules, and multispecific antibodies formed from antibody fragments. The antibody fragments are obtained by conventional techniques. For example, useful binding fragments may be prepared by peptidase digestion of the antibody using papain or pepsin.

"Fv" is the minimum antibody fragment which contains a complete antigen-recognition and antigen-binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

Antibodies of the invention are directed to an antibody of the IgG class from a murine source; however, this is not meant to be a limitation. The above antibody and those antibodies having functional equivalency with the above antibody, whether from a murine source, mammalian source including human, or other sources, or combinations thereof are included within the scope of this invention, as well as other classes such as IgM, IgA, IgE, and the like, including isotypes within such classes. In the case of antibodies, the term "functional equivalency" means that two different antibodies each bind to the same antigenic site on an antigen, in other words, the antibodies compete for binding to the same antigen. The antigen may be on the same or different molecule.

In one embodiment, a stent is disclosed which provides enhanced short-, mid-, and long-term stent performance relative to single component anti-proliferative or anti-inflammatory agent-containing DE stents, where the stent of the present invention includes anti-PDGF, anti-PDGFR, anti-bFGF, and/or anti-bFGFR antibodies, including growth factor-binding fragments thereof, in one or more drug-releasable or drug-eluting coatings. In a related aspect, such an antibody-coated stent suppresses in-growth of smooth muscle cells, while allowing in-growth of normal endothelial cells onto the inner "lumenal" surface of the stent meshwork.

The term "synthetic graft" means any artificial prosthesis having biocompatible characteristics. In one embodiment this includes synthetic grafts made of Dacron (polyethylene terephthalate, PET) or Teflon (ePTFE). In another embodiment, synthetic grafts are composed of polyurethane. In yet a third embodiment, a synthetic graft is composed of an inner layer of meshed polycarbonate urethane and an outer layer of meshed Dacron. Synthetic grafts may be used for end-to-end anastomosis of vessels or for bypass of a diseased vessel segment.

In one embodiment, the implant is a stent. In general, stents can have virtually any structural pattern that is compatible with a bodily lumen in which it is implanted. Typically, a stent is composed of a pattern or network of circumferential rings and longitudinally extending interconnecting structural elements of struts or bar arms. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility.

The stiffness or flexibility of a portion of a stent pattern can depend on the mass of the portion of the stent. The mass of a portion may be varied by varying the width and/or length of a strut or bar arm that makes up the portion. The shorter a strut, the less stiff and more deformable along its length it is. Similarly, the smaller the width of a stent, the less stiff and more deformable along its length it is. Therefore, a portion with a smaller mass may tend to undergo more deformation for a give amount of applied force. By allocating the amount of mass to specific struts, it is possible to create a stent having variable strength with greater strength at the high mass areas.

In addition to the stent pattern, the chemical and mechanical properties of a polymeric material making up a stent may influence a stent's radial strength, recoil, and flexibility. Deformation of portions of a stent during radial expansion may induce crystallization and/or circumferential molecular orientation along the axis of stress. This process is referred to as strain-induced crystallization. Induced crystallization and orientation tend to increase the mechanical strength and rigidity of tube-like section along the direction of orientation of the polymer chains. Therefore, the radial strength and rigidity of a tube-like section may be increased by expansion of the device.

Rearrangement of polymer chains may take place when a polymer is stressed in an elastic region and in a plastic region of the polymer material. A polymer stressed beyond its elastic limit to a plastic region generally retains its stressed configuration and corresponding induced polymer chain alignment when stress is removed. The polymer chains may become oriented in the direction of the applied stress which results in an oriented crystalline structure. Thus, strain-induced crystallization in portions of a stent may result in a permanent increase in strength and modulus in that portion. This is particularly advantageous since after expansion in a lumen, it is generally desirable for a stent to remain rigid and maintain its expanded shape so that it may continue to hold open the lumen.

Furthermore, induced orientation and crystallization of a portion of a stent may increase a $T_g$ of at least a deformed portion. The $T_g$ of the polymer in the device may be increased to above body temperature. Therefore, barriers to polymer chain mobility below $T_g$ may tend to inhibit or prevent loss of induced orientation and crystallization. Thus, a deformed portion may have a high creep resistance and may more effectively resist radial compressive forces and retain the expanded shape during a desired time period.

When a stent undergoes expansion, for example, the deformation in localized portions can result in strain-induced crystallization. Therefore, the localized portions may have a higher strength and modulus after expansion. Additionally, plastic deformation causes the portions to be "locked" in the deformed state. Also, the more the deformation is aligned circumferentially, then the greater the radial strength of the expanded stent due to the strain induced crystallization of the localized portions.

The holes, wells, slots, grooves and the like, described for the device 10 comprising coated surfaces 20 (see FIG. 2), may be formed in the surface 11 of the device 10 by a variety of techniques. For example, such techniques include drilling or cutting by utilizing lasers, electron-beam machining and the like or employing photoresist procedures and etching the desired apertures.

All the bioactive materials discussed above that may be coated on the surface of the device 10 may be used to be contained within the apertures of this aspect of the invention. Likewise, layers of bioactive materials 13,14 and porous layer 15 may be applied and built up on the exterior surfaces of the device 10 as with regard to other aspects of the invention (see, e.g., FIGS. 2 and 3), e.g., ECM molecules of one bioactive layer 13 may be covalently bound to one surface 11 of the device 10, which is covered by another bioactive layer 14, containing anti-growth factor agents, and a porous layer 15, with the porous layer 15 containing anti-inflammatory agents and/or anti-proliferative agents as illustrated in FIG. 2.

Figure 2:
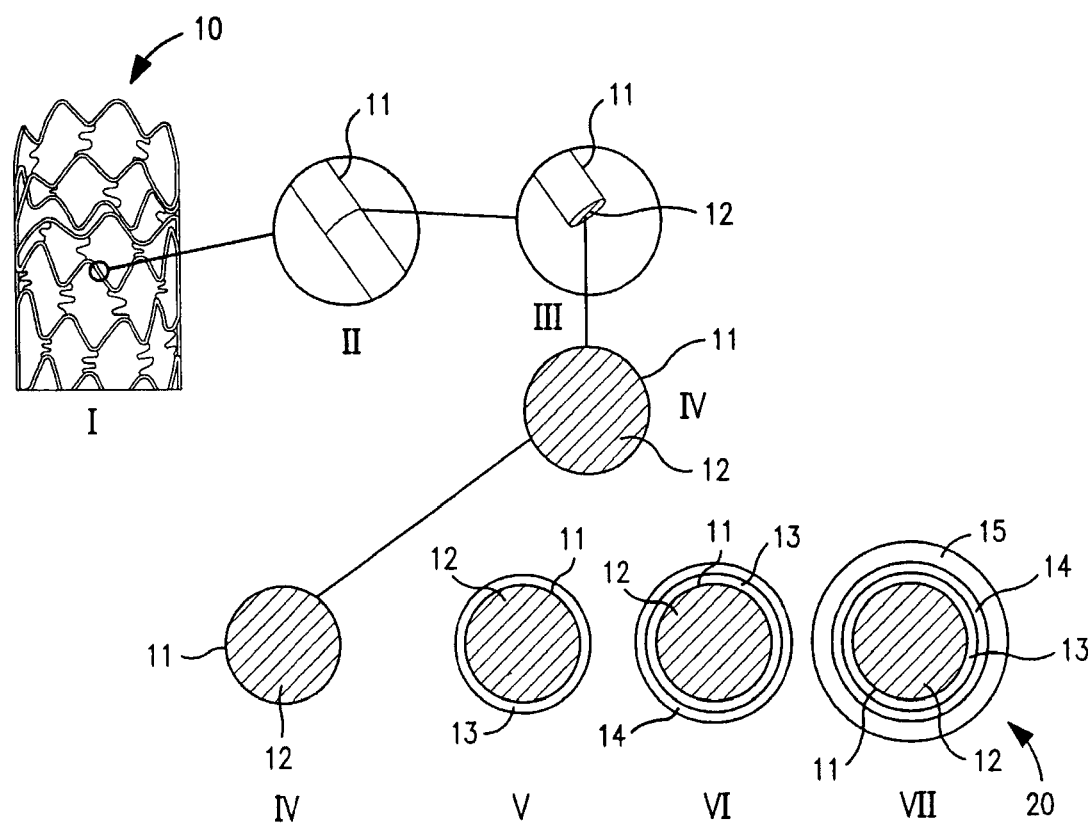
FIG. 2 shows the perspectives and illustrations of FIG. 1 (I)-(IV), including (V) an end view of the metal strut cross section showing a first 13 coating layer, (VI) an end view of the metal strut cross section showing a first 13 and second 14 coating layer, and (VII) an end view of the metal strut cross section showing a first 13, second 14, and third 15 coating layer.
Figure 3:
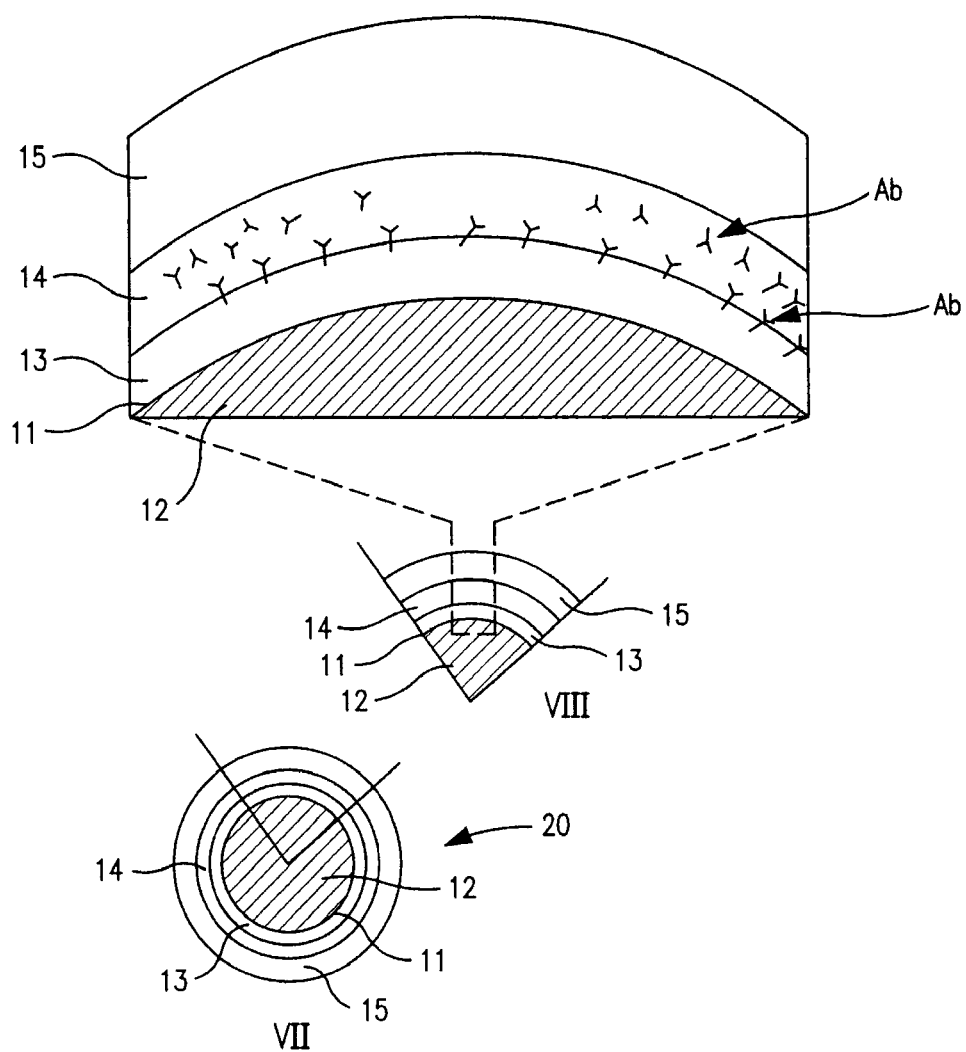
FIG. 3 shows an expanded view of a section (VIII) of a coated surface 20, depicting anti-growth factor antibodies (Ab) (arrows) within a second 14 coating layer, including antibodies intercalating into a first 13 coating layer.

The method of making the implant 10 comprising coated surfaces 20 according to the present invention is provided below (FIG. 2). In its simplest form, the method comprises the steps of depositing the at least one layer 13 of bioactive material over the structure 11, followed by depositing the at least one porous layer 15, for example, by vapor deposition or plasma deposition, over the at least one bioactive material layer 13 or additional bioactive material layer 14 on the one surface of structure 11. The at least one porous layer 15 being composed of a biocompatible polymer and being of a thickness adequate to provide a controlled release of the bioactive materials. The at least one additional bioactive material containing coating layer 14 is first posited by vapor deposition directly on the layer 13 placed on the base material of the structure 11. Such deposition may be carried out by preparing or obtaining di-p-xylylene or a derivative thereof, sublimating and cracking the di-p-xylylene or derivative to yield monomeric p-xylylene or a monomeric derivative, and allowing the monomer to simultaneously condense on and polymerize over the base material 11 to form the at least one layer 13. The deposition step is carried out under vacuum, and the base material 11 or at least one layer 13 is maintained at or near room temperature during the deposition step. The deposition may be carried out in the absence of any solvent or catalyst for the polymer, and in the absence of any other action to aid polymerization.

The additional layer 14 containing the desired bioactive material or materials is then applied onto the first layer 13 which is deposited directly to at least one surface 11 of the structure 10. This application step can be carried out in any of a variety of convenient ways, such as by dipping, rolling, brushing or spraying a fluid mixture of the bioactive material containing layer 14 onto the coating layer 13, or by electrostatic deposition of either a fluid mixture or dry powder of the bioactive material containing layer 14, or by any other appropriate method. Different bioactive agents may be applied to different sections or surfaces of the device.

It may be convenient to apply a mixture of the bioactive material or materials and a volatile fluid over the structure, and then remove the fluid in any suitable way, for example, by allowing it to evaporate. When heparin sulfate proteoglycan or its derivatives serve as the bioactive material(s), the fluid may be ethyl alcohol.

Other methods of depositing the bioactive material layers 13,14 over the structure 11 would be equally useful. Without regard to the method of application, however, what is important is that the bioactive material need only be physically held in place until the porous layer 15 is deposited over it. This may avoid the use of carriers, surfactants, chemical binding and other such methods often employed to hold a bioactive agent on other devices. The additives used in such methods may be toxic, or the additives or methods may alter or degrade the bioactive agent, rendering it less effective, or even toxic itself. Nonetheless, if desired these other methods may also be employed to deposit the bioactive material layers 13,14 of the present invention.

The bioactive material may, of course, be deposited on the one surface of the structure 10 as a smooth film or as a layer of particles. Moreover, multiple but different bioactive materials may be deposited in a manner that different surfaces of the device contain the different bioactive agents. In the latter case, the particle size may affect the properties or characteristics of the device 10 comprising coated surfaces 20, such as the smoothness of the uppermost porous coating 15, the profile of the device 10 comprising coated surfaces 20, the surface area over which the bioactive material layers 13,14 are disposed, the release rate of the bioactive material, the formation of bumps or irregularities in the bioactive material layers 13,14 the uniformity and strength of adhesion of the bioactive material layers 13,14 and other properties or characteristics. For example, it may be useful to employ micronized bioactive materials, that is, materials which have been processed to a small particle size, typically less than 10 μm in diameter. However, the bioactive material may also be deposited as microencapsulated particles, dispersed in liposomes, adsorbed onto or absorbed into small carrier particles, or the like.

The bioactive material may be posited on a surface of structure 10 in a specific geometric pattern. For example, the ends of the device 10 may only contain the bioactive material, or the bioactive material may be applied in parallel lines, particularly where two or more bioactive materials are applied to the same surface.

In any event, once the bioactive material layers 13,14 are in place, the at least one porous layer 15 is then applied over the at least one of the bioactive material layers 13,14 in the same manner as for the application of the coatings 13,14 to the base material 11. A polymer such as parylene or a parylene derivative is applied at the lesser thickness disclosed above, however, so as to yield the at least one porous layer 15, where the at least one porous layer 15 may comprise one or more anti-inflammatory and/or anti-proliferative agents.

Any other layers, are applied in the appropriate order and in the same manner as disclosed above. The steps of the method are preferably carried out with any of the bioactive materials, structures, and base materials disclosed above.

Of course, polyimide may be deposited as any or all of the coating layers 13,14,15 by vapor deposition in a manner similar to that disclosed above. Techniques for the plasma deposition of polymers such as poly(ethylene oxide), poly(ethylene glycol), poly(propylene oxide), silicone, or a polymer of methane, tetrafluoroethylene or tetramethyl-disiloxane on other objects are well-known, and these techniques may be useful in the practice of the present invention.

One technique for controlling the release of the bioactive material may include depositing monodispersed polymeric particles, i.e., referred to as porogens, on the surface of the device 10 comprising one or more coatings 13,14 containing bioactive materials prior to deposition of porous layer 15. After the porous layer 15 is deposited and cured, the porogens may be dissolved away with the appropriate solvent, leaving a cavity or pore in the outer coating to facilitate the passage of the underlying bioactive materials.

The method can further entail carrying out the depositing steps with the various embodiments of the device 10 comprising coated surfaces 20 disclosed above, in accordance with the method of making the device 10 comprising coated surfaces 20 disclosed above. More particularly, the step of depositing the at least one porous layer 15 can comprise polymerizing at least one layer 13,14 from a monomer vapor, including a vapor of parylene or a parylene derivative, free of any solvent or catalyst.

The method of treatment according to the present invention is completed by inserting the device 10 comprising coated surfaces 20 into the vascular system of the patient. The at least one porous layer 15 and/or any additional porous layers automatically release the bioactive material or materials in a controlled fashion into the patient.

The following examples are intended to illustrate but not limit the invention.

EXAMPLE 1

Agents: Paclitaxel, Sirolimus, Fibronectin, and Anti-Growth Factor Monoclonal Antibody.

Delivery Methods:

1. Experimental Stent Delivery Method—Delivery from Polymer Matrix:

Solutions of the agents for the different layers, prepared in a solvent miscible with polymer carrier solution, are mixed with solution of polymer at final concentration range 0.001 weight % to 30 weight % of paclitaxel and sirolimus. Polymers are biocompatible (i.e., not elicit any negative tissue reaction or promote mural thrombus formation) and degradable, such as lactone-based polyesters or copolyesters, e.g., polylactide, polycaprolacton-glycolide, polyorthoesters, polyanhydrides; poly-amino acids; polysaccharides; poly-phosphazenes; poly(ether-ester) copolymers, e.g., PEO-PLLA, or blends thereof. Nonabsorbable biocompatible polymers are also suitable candidates. Polymers such as polydimethylsiolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters.

Polymer/drug mixtures are applied to the surfaces of the coated stent by either dip-coating, or spray coating, or brush coating or dip/spin coating or combinations thereof, and the solvent allowed to evaporate to leave a film with entrapped paclitaxel and sirolimus.

2. Stent Preparation: Anti-Growth Coating

Stents will be made from 316L stainless steel and will be cleaned and passivated by first washing in an anionic detergent in an ultrasonic cleaner and then soaked in hot nitric acid with agitation, followed by a final deionized water rinse.

Derivatized stents will be prepared as follows—stents will be dipped into a 2% mixture of N-(2-aminoethyl-3-aminopropyl) trimethoxysilane in 95% ethanol for three minutes, removed, air dried at room temperature and then cured for 10 minutes at 110° C.

Polyethylene glycol (PEG) Spacer Coupling—Derivatized stents will be placed in 100 ml of 0.1 M MES buffer containing 10 mM Dicarboxymethyl-PEG and 500 mg of EDC added and incubated at 25° C. with constant stirring for two hours.

Tethered Antibody—Antibodies to growth factors will be immobilized to the PEG functionalized stents in a one-step carbodiimide coupling reaction by immersing the stents into 150 ml of 0.1 M MES buffer (pH 4.5) into which 1.0 mg of anti-PDGFR antibody, anti-bFGF antibody, or anti-FGFR antibody is dissolved and incubated at 25° C. for two hours. Stents will be removed from the solution and rinsed five times with 50 ml of phosphate buffered saline (pH 7.2) with 0.02% Tween 20.

Reagents include: N-(2-aminoethyl-3-aminopropyl)trimethoxysilane (Degussa-Huls); MES buffer—morpholine ethane sulfonic acid buffer (Sigma, St. Louis, Mo.); EDC-1-ethyl-3-(3-dimethylaminopropyl) carbodiimide (Sigma, St. Louis, Mo.); Dicarboxymethyl-PEG Dicarboxymethyl-poly(ethylene glycol) [MW 3400] (Shearwater, Huntsville, Ala.).

ECM molecules (i.e., heparin sulfate proteoglycan) may be tethered to the inner lumenal surface of the stent as described above, or tethered to the bound antibody or vice versa.

Although the invention has been described with reference to the above examples, it will be understood that modifications and variations are encompassed within the spirit and scope of the invention. Accordingly, the invention is limited only by the following claims.

What is claimed is:

1. A tubular vascular implant composed of a metal, an alloy or a biostable polymer substrate, the implant comprising;
    a) an outer layer coating comprising an anti-proliferative agent, an anti-inflammatory agent, or combination thereof;
    b) a middle layer comprising at least one anti-growth factor agent, wherein the middle layer is formulated for delayed and sustained release of the at least one anti-growth factor agent; and
    b) a bottom layer coating comprising at least one non-thrombogenic extracellular matrix (ntECM) molecule;
    wherein the at least one ntECM molecule is fibronectin, wherein the outer layer coating is formulated for immediate and sustained release of the anti-proliferative agent or the anti-inflammatory agent upon implantation, wherein the at least one ntECM molecule is permanently affixed to the lumen or interstices of the implant, and wherein the implant promotes in-growth of endothelial cells and inhibits restenosis in biological tissue.

2. The tubular vascular implant of claim 1, wherein the middle layer coating intercalates into the bottom layer.

3. The tubular vascular implant of claim 2, wherein the at least one anti-growth factor agent is covalently bound to one or more surfaces of the implant.

4. The tubular vascular implant of claim 1, wherein the at least one anti-growth factor agent is covalently bound to one or more polymers coating the implant.

5. The tubular vascular implant of claim 1, wherein the anti-proliferative agent is selected from the group consisting of paclitaxel, actinomycin, a taxane, daunorubicin, methotrexate, cyclophosphamide, bleomycin, busufane, 5-fluorouracil, cisplatin, vinblastine, vincristine, epothilones, methotrexate, azathioprine, halofuginone, adriamycin, actinomycin and mutamycin; endostatin, angiostatin, and thymidine kinase inhibitors.

6. The tubular vascular implant of claim 5, wherein the anti-proliferative agent is paclitaxel.

7. The tubular vascular implant of claim 1, wherein the anti-inflammatory agent is a calcineurin inhibitor.

8. The tubular vascular implant of claim 7, wherein the anti-inflammatory agent is selected from the group consisting of sirolimus, tacrolimus, everolimus, and zotatrolimus.

9. The tubular vascular implant of claim 8, wherein the anti-inflammatory agent is sirolimus.

10. The tubular vascular implant of claim 1, wherein the at least one anti-growth agent is selected from the group consisting of an anti-PDGF polyclonal or monoclonal antibody or a PDGF-binding fragment thereof, an anti-PDGFR polyclonal or monoclonal antibody or a PDGFR-binding fragment thereof, an anti-bFGF polyclonal or monoclonal antibody or a bFGF-binding fragment thereof, and an anti-FGFR polyclonal or monoclonal antibody or an FGFR-binding fragment thereof, or a combination thereof.

11. The tubular vascular implant of claim 10, wherein the at least one anti-growth agent is an anti-PDGF monoclonal antibody or a PDGF binding fragment thereof.

12. The tubular vascular implant of claim 10, wherein the at least one anti-growth agent is an anti-bFGF or anti-FGFR monoclonal antibody or a bFGF- or FGFR-binding fragment thereof.

13. The tubular vascular implant of claim 10, wherein the bottom layer coating further comprises laminen, heparin, heparin sulfate proteoglycan (HSP), elastin, chondroitin, or a combination thereof.

* * * * *